(12) United States Patent
Dahlmann

(10) Patent No.: US 11,406,135 B2
(45) Date of Patent: Aug. 9, 2022

(54) ELECTRONIC CIGARETTE

(71) Applicant: INNOCIGS GMBH & CO. KG, Hamburg (DE)

(72) Inventor: Dustin Dahlmann, Hamburg (DE)

(73) Assignee: INNOCIGS GMBH & CO. KG, Hamburg (DE)

( * ) Notice: Subject to any disclaimer, the term of this patent is extended or adjusted under 35 U.S.C. 154(b) by 475 days.

(21) Appl. No.: 16/291,760

(22) Filed: Mar. 4, 2019

(65) Prior Publication Data

US 2019/0269176 A1 Sep. 5, 2019

(30) Foreign Application Priority Data

Mar. 5, 2018 (EP) ..................................... 18159863

(51) Int. Cl.
*A61M 11/04* (2006.01)
*A24F 40/51* (2020.01)
(Continued)

(52) U.S. Cl.
CPC .............. *A24F 40/51* (2020.01); *A24F 40/42* (2020.01); *A61M 11/042* (2014.02); *G01F 23/247* (2013.01); *G01F 23/265* (2013.01); *A24F 40/10* (2020.01); *A24F 40/60* (2020.01); *A61M 2205/3317* (2013.01); *A61M 2205/3368* (2013.01); *A61M 2205/3386* (2013.01); *A61M 2205/3653* (2013.01); *A61M 2205/502* (2013.01); *A61M 2205/581* (2013.01); *A61M 2205/587* (2013.01)

(58) Field of Classification Search
CPC ........ A61M 11/042; A61M 2205/3317; A61M 2205/3368; A61M 2205/3386; A61M 2205/3653
See application file for complete search history.

(56) References Cited

U.S. PATENT DOCUMENTS 4,092,860 A * 6/1978 Arts .................... A61M 1/78
73/304 R
6,155,268 A * 12/2000 Takeuchi .............. A24F 40/485
131/273
(Continued)

FOREIGN PATENT DOCUMENTS

CN  1205849  1/1999
CN  105658100  6/2016
(Continued)

*Primary Examiner* — Bradley J Osinski
(74) *Attorney, Agent, or Firm* — Price Heneveld LLP

(57) ABSTRACT

A vaporizing device for consuming a stimulant or a pharmaceutical substance by inhaling a vapour comprise a housing having an exit opening provided at one end of said housing, a vaporizer connected to said exit opening via a vapour conduit, said vaporizer having an electrically driven heating unit and a liquid exposure section that is heated by the heating unit to vaporize a liquid in said liquid exposure section, a liquid reservoir connected to said liquid exposure section via a liquid conduit, and an electrical energy storage unit electrically connected to said heating unit, wherein an electrical fluid level sensor is associated with said liquid reservoir, said fluid level sensor being arranged and adapted to produce a low-level-signal if the liquid level within said liquid reservoir is below a predetermined threshold.

19 Claims, 2 Drawing Sheets

(51) Int. Cl.
*G01F 23/24* (2006.01)
*G01F 23/263* (2022.01)
*A24F 40/42* (2020.01)
*A24F 40/10* (2020.01)
*A24F 40/60* (2020.01)

(56) References Cited

U.S. PATENT DOCUMENTS

| 2017/0245551 | A1* | 8/2017 | Reevell | G01F 23/22 |
| 2019/0029321 | A1* | 1/2019 | Borkovec | A24F 1/30 |

FOREIGN PATENT DOCUMENTS

| EP | 3192381 | 7/2017 |
| WO | 2015026948 | 2/2015 |
| WO | 2016101202 | 6/2016 |
| WO | 2017045897 | 3/2017 |
| WO | 2017121546 | 7/2017 |

* cited by examiner

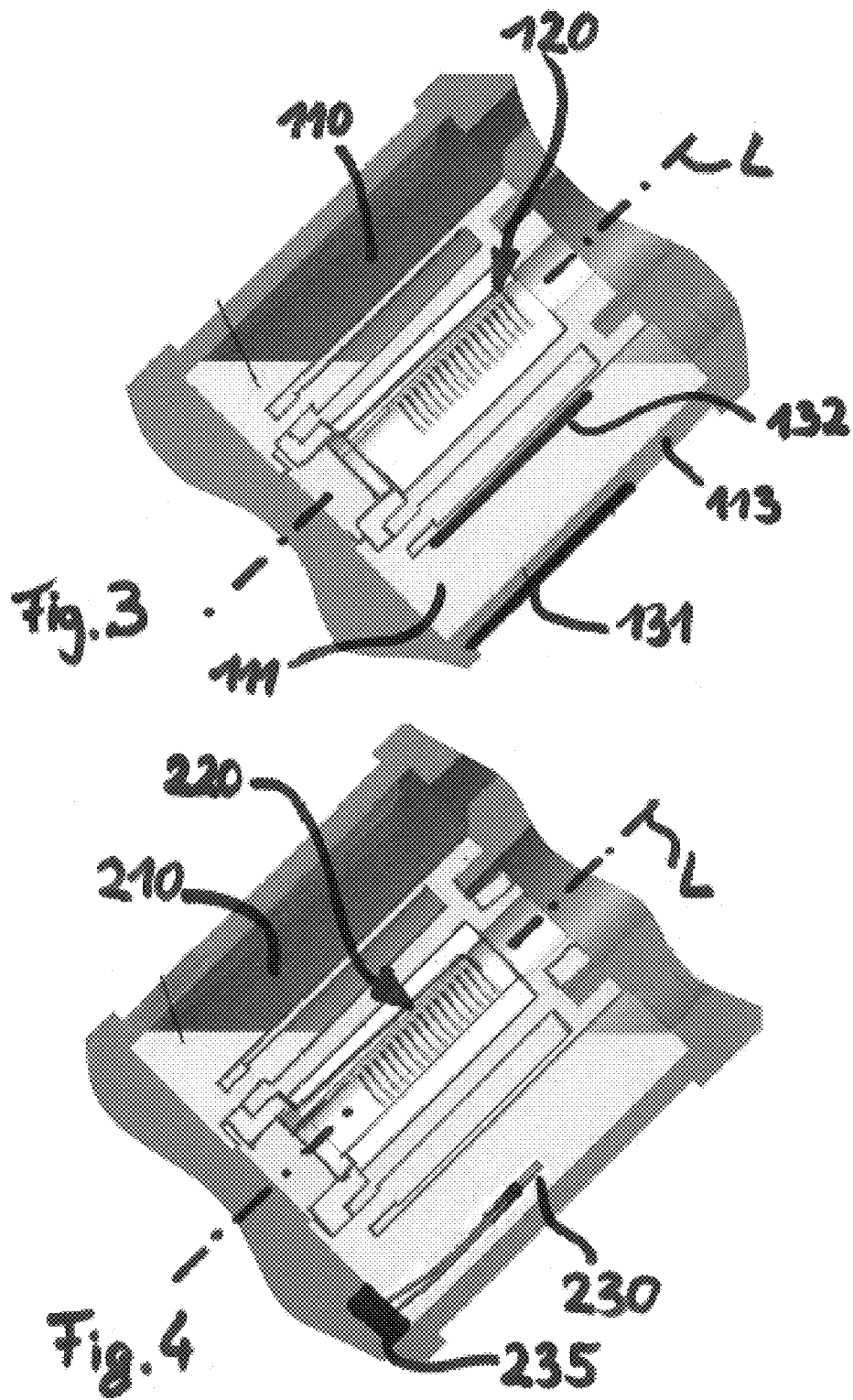

ELECTRONIC CIGARETTE

CROSS-REFERENCE TO FOREIGN PRIORITY APPLICATION

The present application claims the benefit under 35 U.S.C. §§ 119(b), 119(e), 120, and/or 365(c) of EP 18159863.2 filed Mar. 5, 2018.

FIELD OF THE INVENTION

The invention relates to a vaporizing device for consuming a stimulant or a pharmaceutical substance by inhaling a vapor, comprising a housing that incorporates an exit opening provided at one end of said housing, a vaporizer connected to said exit opening via a vapour conduit, said vaporizer having an electrically driven heating unit and a liquid exposure section which is heated by the heating unit to vaporize a liquid in said liquid exposure section, a liquid reservoir connected to said liquid exposure section via a liquid conduit, and an electrical energy storage unit electrically connected to said heating unit.

BACKGROUND OF THE INVENTION

Vaporizing devices of such type are known as electronic cigarettes and as such serve to provide a stimulant by vaporizing a liquid and allowing a user to inhale said vaporized liquid. The vaporizing device is often designed as a cylindrical body having a mouthpiece at one end which is in fluid communication with the exit opening and allowing the user to hold the vaporizing device like a regular tobacco cigarette. Vaporizing devices of the aforementioned type may furthermore be used for inhaling pharmaceutical substances which are then transferred into the lung of the patient and absorbed by the body via transfer in the lung of the patient.

Generally, such vaporizing devices comprise a vaporizer with an electrically driven heating unit which may be embodied as a heating wire which is heated by an electrical current flowing through said wire and inducing resistance heating. Instead, other heating elements, like ceramic elements, may be employed to produce the heat required for vaporizing the fluid. The fluid is transferred from a liquid reservoir serving as a tank and brought into said liquid exposure section to be in a close relationship to the heating unit. In said liquid exposure section, the liquid is transferred from the liquid state into a vaporized state or in a state of multiple small liquid droplets which can be released by a stream of air. The droplets and the air are heated by the heating wire thus producing either a stream of air/vapour mixture or a stream of air/droplets or a mixture thereof which is then inhaled by the user. The vaporizer is thus understood as a heating component for heating the mixture of air, vapour, and/or droplets which is inhaled by the user and it is of importance for the convenience of the user that this mixture is inhaled at an elevated temperature.

The heating device is supplied with electrical energy out of an electrical energy storage device, e.g., a replaceable battery or a rechargeable battery. The electrical energy storage device can be replaced or recharged if it is empty. By this, the whole vaporizing device is independent from an external energy supply during use but may be refilled with liquid or with energy.

The liquid reservoir which serves as a liquid storage unit may be embodied in different design options. Generally, the liquid reservoir may be embodied as a bottle or tank assembly which has an outer wall defining an inner space for taking up the liquid inside and which can be coupled to the vaporizer via a supply opening and a supply channel or the like. The liquid reservoir may be incorporated into the vaporizing device as a fixed component which can be refilled from outside through a refill opening by introducing liquid into the liquid reservoir. As an alternative, the liquid reservoir may be a replaceable part similar to an ink cartridge and in such case can be replaced if it is empty by a new, full cartridge. In some embodiments, the liquid reservoir may be filled with an open porous material which absorbs the liquid and releases the liquid to the vaporizer, e.g., filled with an absorbent cotton, a fiber material, or the like.

The quality of the mixture of air, vapour, and/or droplets inhaled by the user depends on several parameters. Two important parameters are the amount of heat supplied by the heating device and the amount of liquid supplied to the vaporizer. Generally, the amount of heat and the amount of liquid should be in a specific relation to each other or within a specific range of relation to each other to prevent overheating or too little heating of the liquid in the vaporizer. Further, some vaporizer designs are sensitive to a too little supply of liquid and then tend to overheat and produce a deterioration of the heating device itself or any material in close neighbourhood thereto.

SUMMARY OF THE INVENTION

It is an object of the invention to provide a vaporizing device which is able to better control the heating process of the liquid in the vaporizer.

This object is solved by a vaporizing device as described in the introductory portion and which is characterized by an electrical fluid level sensor associated with said liquid reservoir, said fluid level sensor being arranged and adapted to produce a low-level-signal if the liquid level within said liquid reservoir is below a predetermined threshold.

According to the invention, an electrical fluid level sensor is provided to measure the fluid level in the liquid reservoir or to produce a signal related to said fluid level. By such an electrical fluid level sensor either (1) the fluid level in the liquid reservoir can be detected and thus may be used to control the vaporizer such that in case of a low level of liquid in the liquid reservoir the vaporizer may be controlled such as to adapt the amount of heating to such low level of liquid; or (2) to interrupt the heating process in the vaporizer.

An aspect of the invention is related to the fact that the fluid level sensor produces a signal related to the fluid level in the liquid reservoir. Since the vaporizing device is, in particular, used like an electronic cigarette and thus may be used in different orientations of the liquid reservoir in relation to the direction of gravity, the level of the fluid in the liquid reservoir may be different and may, in particular, be such that no sufficient supply of fluid to the vaporizer takes place, even though the liquid reservoir still is filled to a certain degree with a liquid. Thus, the level detected by the fluid level sensor is a characteristic parameter for controlling the heating in the vaporizer to avoid overheating in any such low- or no-supply condition, which may depend on an empty liquid reservoir or a specific, unusual orientation of the vaporizing device in relation to the direction of gravity. Thus, in contrast to sensors which merely indicate the remaining liquid volume in the liquid reservoir, the filling ratio, or the like, the fluid level sensor according to the invention is specifically adapted to produce the low-level-signal depending on a specific predetermined threshold of the liquid level being no longer present. This specific liquid level thus can be defined by the arrangement of the fluid level sensor such that the low-level-signal is produced by the fluid level sensor in case of a too little volume of liquid in the liquid reservoir or in case of an orientation of the liquid reservoir where insufficient liquid is supplied to the vaporizer although the liquid reservoir may still be sufficiently filled with liquid.

The housing of the vaporizing device is understood to be a one-part housing, i.e., an integral housing including all components of the device or to be a housing with two, three, or more housing components which are connected to each other. In particular, components like the liquid reservoir or the electrical energy storage unit may have a separate housing component or may incorporate its own housing and then be coupled to a housing which includes other components of the vaporizing device.

Beside the use of the low-level-signal for controlling the vaporizer, the low-level-signal may further be used to indicate to a user that the amount of liquid in the liquid reservoir is no longer sufficient or a refilling or replacement of the liquid reservoir should be done soon or to indicate that the orientation of the vaporizing device is not providing a proper liquid level for supply of the vaporizer and thus the user is motivated to change the orientation of the device.

According to the invention, an electrical fluid level sensor is used to detect the level of liquid in the liquid reservoir. By this, a sensor outputting an electric signal is employed according to the invention. This allows to process the sensor signal for a direct control of the vaporizer in an electric control circuit. In particular, a direct control of the heating unit of the vaporizer to prevent overheating in case of insufficient supply of liquid due to low level liquid in the liquid reservoir is possible. Thus, in contrast to a fluid level sensor which is merely employed and adapted to signalize the liquid level in the liquid reservoir to a user to allow the user to decide whether liquid shall be refilled or not, the fluid level sensor according to the invention can be integrated into the control circuit of the vaporizing device and its signal can be processed therein.

According to a first preferred embodiment of the invention the housing extends in a longitudinal direction along a longitudinal axis, wherein the exit opening is arranged at one end of said housing with respect to said longitudinal axis and the fluid level sensor is adapted and arranged to produce said low-level signal if the level inside said liquid reservoir falls below said minimum level threshold with the housing being oriented in a usual operational alignment range, said usual operational alignment range being defined by an orientation of said longitudinal axis in an angular range of +/−45° or +/−30° in relation to a horizontal plane. The usual operational alignment range may further be variable with regard to an angular rotation about said longitudinal axis by up to 360°. In some embodiments, the angular rotation about said longitudinal axis may, however, be somewhat limited, e.g., by the shape of the housing or by a functional characteristic, such as a button to be pushed by the user. In such case, the angular rotation may be limited to +/−45°, +/−35°, or +/−15° in relation to a regular angular position about said longitudinal axis. As explained in the introductory part, the housing, which may be a one-part or multipart housing, may have a general elongated form which is similar to a tobacco cigar or cigarette, thus defining a longitudinal axis in the direction of the main extension of the housing. In use, the vaporizing device thus may be oriented to point slightly downward with the tip at the opposite end of the mouthpiece incorporating the exit opening or may point slightly upward with said tip, of which both are orientations in relation to the direction of gravity which may occur in regular use. In particular, if a liquid reservoir is used which is taking up the liquid in an empty, non-filled space, i.e., without any open porous material inside the liquid reservoir, the orientation of the vaporizing device will influence the position and the orientation of the level of liquid inside the liquid reservoir. Thus, the signal of the fluid level sensor may be influenced by said orientation of the whole vaporizing device. According to this embodiment, the fluid level sensor is arranged and adapted to operate within a certain range of orientation of the vaporizing device, namely, the housing, which is defined by a certain orientation of the device, namely the longitudinal axis, with respect to a swivel angle in relation to a horizontal plane and with respect to a rotational angle about the longitudinal axis of the housing. By this, the fluid level sensor will safely detect an insufficient amount of liquid in the liquid reservoir on the basis of detecting the level of the liquid within a certain range of orientation of the housing with respect to two rotational axes perpendicular to each other and the fluid level sensor may further indicate the fluid level falling below the threshold in case of an angular rotation about said longitudinal axis or an orientation in relation to the horizontal plane which is outside of said range of regular operational alignment.

It is understood that the orientation of said longitudinal axis in relation to the horizontal plane may be a smaller range than +/−30°, for example +/−25°, +/−20°, or +/−15° or may be a larger range than the said range, for example +/−40°, +/−50°, or even +/−60°. In the same way, the angular rotation about the longitudinal axis may be smaller or larger than the said range of +/−15°, e.g. +/−10°, +/−5°, or +/−20°, +/−25°, +/−30°, or even +/−45°.

According to a further preferred embodiment the vaporizing device may be further improved by a control unit coupled to said fluid level sensor and to said heating unit for signal transmission, wherein said control unit is adapted to reduce the supply of electrical energy by al least 40%, in particular, to stop the supply of electrical energy to the heating device if the control unit receives said low-level-signal from said fluid level sensor. According to this embodiment the low-level-signal produced by the fluid level sensor is used to control the supply of electrical energy to the vaporizer. By this, the heating device of the vaporizer can be supplied with less or even no electrical energy in case of a low liquid level being detected by the fluid level sensor in the liquid reservoir to prevent overheating of the vaporizer. It is understood that beside a one-step reduction by, e.g., 40%, the electrical energy may be reduced by a larger amount, i.e., by 60% or even 80%, such that the heating device is supplied with only 40% or even 20% of electrical energy when compared to a regular operation or the reduction of supply of electrical energy may be reduced by less than 40%, e.g., by only 30% or only 20%, such that the heating device is driven with 70% or 80% of the electrical energy in regular operational condition. Furthermore, a two-step or multistep reduction may be employed, such that the energy is reduced in a first step by a certain percentage and in a second step by an additional certain percentage and in possible further steps by further percentages. The steps may depend on the duration of the presence of the low-level-signal such that in case of the presence of the low-level-signal for more than two seconds the second step of energy reduction is made and so on. Alternatively or additionally, the fluid level sensor may be adapted to detect the liquid level in the liquid reservoir to fall under a first threshold and to fall under a second, lower threshold. A first threshold and the energy reduction may depend on the presence of a low-level-signal signalizing falling of the liquid level under the first threshold and a second low-level-signal signalizing the liquid level falling under the second threshold.

According to a further preferred embodiment, the vaporizing device may comprise a control unit arranged inside said housing and coupled to said fluid level sensor and to an optical or acoustical user interface for signal transmission, wherein said control unit is adapted to control said optical or acoustical user interface for outputting an optical or acoustical signal, respectively, upon receipt of said low-level-sensor by said control unit. According to this embodiment, the low-level-sensor produced by the fluid level sensor may be used to produce a signal to the user which indicates the presence of a low liquid level in the liquid reservoir, I e.g., an optical signal, acoustical signal, or both. It is understood that this user interface signal may be the only signal produced by the device in reaction to detection of a low liquid level or may be an additional measure taken beside a control of the heating device or the like upon detection of a low liquid level by the fluid level sensor.

It is further preferred that said fluid level sensor is a sensor working under the principle of a capacity detecting sensor forming a capacitor, wherein said capacity is dependent from said fluid level in said liquid reservoir. According to this embodiment, the sensor comprises a capacitor, which capacity is changed by a change of the amount of liquid in said liquid reservoir. The sensor thus is working to measure a capacity of said capacitor, indicating the level of liquid in the liquid reservoir. Generally, different setups of such a sensor according to the principle of a capacitor are applicable. Where the fluid to be detected is an electrically conducting fluid, the fluid itself may form an electrode of the capacitor and thus the sensor may be designed such as to detect a change of capacity depending on the size of the electrode formed by the liquid. In another setup, the liquid to be detected may form an insulator of a capacitor formed by two electrically conducting electrode and a change in the amount of liquid in the liquid reservoir may effect a change in the insulating efficiency of the capacitor—thus resulting in a change in capacity to be measured.

It is understood that such a capacitor generally comprises a ground electrode, a measuring electrode embodied as electrical conductor element, and an insulating component between the two electrodes, wherein the fluid itself may form one of said electrodes. The fluid itself may alternatively form the insulating component or may partially form the insulating component in that an insulating interspace is fully or partially filled by the fluid.

Still further, a shield electrode may be provided to reduce any external factors influencing the capacity of the capacitor. Still further, a compensating electrode may be arranged adjacent the measuring electrode to compensate any error in measurement caused by deposit or debris on said electrodes.

According to a further preferred embodiment said fluid level sensor comprises at least one electrical conductor element and a further electrical conductor element and said fluid level sensor is adapted to determine a capacity of a capacitor defined by a first electrode formed by said electrical conductor element, a second electrode formed by said further electrical conductor and an electrically insulating space arranged between said first and second electrode, wherein the low level sensor is adapted to detect a capacity of said capacitor and the low-level-signal is generated depending on said capacity falling below a predetermined minimum threshold or rising above a predetermined maximum threshold, wherein said insulating space is at least partially provided by a region of said liquid reservoir. According to this embodiment, an electrical conductor element and a further electrical conductor is provided which are spaced from each other by an electrically insulating space. By this, a capacitor is built up and the fluid level sensor is adapted to detect the capacity of said capacitor. The electrically insulating space is at least partially provided by a region of the liquid reservoir and thus filled by the liquid in the liquid reservoir depending on the level of said liquid in the liquid reservoir. By this, the level of the liquid reservoir influences the insulating properties and thus the capacity of the capacitor because the electrical characteristics of the liquid are different from the electrical characteristics of air. It is understood that the liquid may be electrically insulating or may be an electrical conductor. In the latter case, the further electrical conductor may be formed by the liquid in the liquid reservoir itself and thus the capacity of the capacitor is influenced by the volume of said electrical conductor (defining the size of the second electrode) rather than by the electrical insulating space. In this embodiment, the liquid shall be in contact with a further electrical conductor component to establish an electrical contact to the liquid, whereby the fluid level sensor is electrically connected to said further electrical component and via said further electrical component to the liquid itself. In case that the liquid is an electrical insulator, the further electrical conductor may be provided by a separate component positioned in a distance to the electrical conductor element and the liquid may form part of the electrically insulating space between the conductor element and the further electrical conductor. It is understood that the electrical conductor element may in particular be formed such as to be a component with a surface extending over a circumferential region of the liquid reservoir, e.g. in case that the liquid reservoir is of cylindrical shape the electrical conductor element may be formed by a plate or foil with a semi-circular cross section extending across 180° of the liquid reservoir or any other so-formed foil or plate extending across a larger or smaller angular range like e.g. 120°, 90°, or less.

It is particularly preferred that said first and second electrodes are arranged inside said liquid reservoir and in direct contact with said liquid, separated and electrically insulated by said electrically insulating space, and wherein said fluid level sensor is adapted to measure a capacity of a capacitor defined by said two electrical conductor elements and said electrically insulating space wherein the low-level-signal is generated depending on said capacity falling below a predetermined minimum threshold or rising above a predetermined maximum threshold, wherein said insulating space is at least partially filled by liquid inside said liquid reservoir. In this embodiment, both electrical conductors of the capacitor are arranged inside the liquid reservoir and are in direct electrical contact with the liquid. This embodiment is particularly suited for measuring the level of electrically insulating liquids in that the liquid volume and thus the level of the liquid inside the liquid reservoir will affect the insulating function of the capacitor and thus the capacity.

In an alternative solution hereto it is particularly preferred that said first and second electrodes are arranged inside or outside said liquid reservoir and are insulated from said liquid and separated by a space, and wherein said fluid level sensor is adapted to measure a capacity of a capacitor defined by said electrodes and said electrically insulating space wherein the low-level-signal is generated depending on said capacity falling below a predetermined minimum threshold or rising above a predetermined maximum threshold, wherein said space is at least partially filled by liquid inside said liquid reservoir. In this embodiment, both electrical conductors of the capacitor are electrically insulated by an isolating arrangement from the liquid in the liquid reservoir and thus are in no direct electrical contact with the liquid. This embodiment is particularly suited for measuring the level of electrically conducting or insulating liquids in that the liquid volume and thus the level of the liquid inside the liquid reservoir will affect the insulating function of the capacitor and thus the capacity.

According to a further preferred embodiment said fluid level sensor comprises a first electrical conductor element arranged adjacent to said liquid reservoir and is electrically insulated from said liquid inside said liquid reservoir to form a first electrode of a capacitor and wherein a further electrical conductor is provided by a further conductor element being in direct electrical contact with said liquid contained in said liquid reservoir to form a second electrode of said capacitor, wherein the low level sensor is adapted to detect a capacity of said capacitor and wherein the low-level-signal is generated depending on said capacity falling below a predetermined minimum threshold or rising above a predetermined maximum threshold, wherein said insulating space is at least partially provided by a region of said liquid reservoir.

According to this specific embodiment an electrical conductor element is arranged which may be positioned inside or outside of the liquid reservoir and which is electrically insulated from the liquid inside said reservoir to form a first electrode of a capacitor. A further electrical conductor is arranged inside the liquid reservoir and is in direct electrical contact to the liquid such that the further electrical conductor and the liquid itself may form a second electrode of said capacitor. In this embodiment, the liquid may be electrically conductive or electrically insulating and the provision of the fluid level sensor in the said arrangement will allow to detect a fluid level in both cases. In the first case with an electrically conductive liquid the amount of liquid will affect the size of one of the electrodes of the capacitor whereas in the latter case with an electrically insulating liquid the amount of liquid and the level of the liquid inside the liquid reservoir will affect the insulating function of the capacitor and thus its capacity.

According to a further preferred embodiment wherein an electrode of said capacitor is provided by an electrical plane element, or wherein a first and a second electrode of said capacitor are provided by at least two electrical plane elements, respectively, wherein an electrical plane element is preferably constituted by a metallic sheet or a metallic foil. According to this embodiment, the single or the two electrical conductor elements are provided as electrical plane elements, i.e. as a flat, planar element with a main extension in two perpendicular directions. The such formed electrical conductor element may be curved or plane, in particular, it may have a semi-cylindrical or partial cylindrical form to be arranged around a part of a cylindrical liquid reservoir or to be arranged inside such a cylindrical reservoir adjacent to the wall of the liquid reservoir.

It is further preferred that a first and second electrode of said capacitor are arranged in a parallel arrangement to each other, in particular where said first and second electrode are arranged in a concentrical arrangement about an axis, wherein said axis is preferably said longitudinal axis. Such a parallel arrangement is understood such that the two electrodes are separated by a layer with constant thickness. This arrangement may be achieved by the two electrical conductors being arranged concentrically about a common axis and in a distance to each other or may be arranged as planar elements in a parallel arrangement and a distance to each other.

It is further preferred that at least one of a first and a second electrode of said capacitor, preferably two or all conductor elements forming said electrodes are positioned inside said liquid reservoir and are in direct electrical contact with said liquid inside said liquid reservoir. According to this embodiment, one, two, three or more, in particular all conductor elements forming the electrodes are positioned inside the liquid reservoir in direct electrical contact to the liquid. By this arrangement, the electrical conductor elements may form a capacitor formed by multiple conductor elements which may, e.g., be wound about each other to form a spiral cross-sectional arrangement, wherein the liquid forms the insulator of the capacitor and thus a precise measurement of the level of the liquid is possible.

It is further preferred that said liquid reservoir comprises a section with a cylindrical shape about a longitudinal axis of said liquid reservoir, wherein at least one of said electrical conductor elements, preferably two or all of said conductor elements each form a cylindrical shell about said longitudinal axis of said liquid reservoir. According to this embodiment, the liquid reservoir has a cylindrical shape or at least comprises a section with such a cylindrical shape, and the fluid level sensor is positioned in said cylindrically shaped section of the liquid reservoir. By such an embodiment, the liquid reservoir can be well integrated into a housing with a cylindrical shape having a design comparable to a conventional tobacco cigarette, and the fluid level sensor is adapted to fulfil its function within such a liquid reservoir in that the single, two, or all conductor elements form a cylindrical shell about the longitudinal axis of the cylindrical liquid reservoir. It is understood that said shell may extend about an angle of 360° about said axis or a smaller angle like 180°, 90°. Preferably, the electrical conductor elements are positioned in the same angular range about said axis.

According to an alternative embodiment of a fluid level sensor it is preferred that said liquid level sensor comprises at least one semiconductor element, wherein said liquid level sensor is adapted to determine a resistance of said semiconductor element and to output said low-level-signal depending on said resistance falling below a predetermined minimum threshold or rising above a predetermined maximum threshold, wherein said semiconductor element is electrically connected to said electrical energy storage unit and is supplied with electrical energy. According to this embodiment, the fluid level sensor is provided by a semiconductor element which is in thermal contact with the liquid. The semiconductor element is supplied with current out of the electrical energy storage unit of the vaporizing device such that the semiconductor element is heated. The semiconductor element is arranged inside the liquid reservoir to be in thermal contact with the liquid if the liquid is above a certain level threshold such that the semiconductor element is experiencing a cooling effect by said liquid if it is immersed into the liquid. In case the liquid falls below said level threshold, this cooling effect is no longer present and thus the semiconductor element will heat up to a higher temperature than if it was immersed into the liquid. This will change the electrical resistance inside the semiconductor element and thus the electrical resistance can be measured to be an indicator of whether the semiconductor element is immersed into the liquid or not. By this, an at least digital measurement of whether the semiconductor element is above or below the liquid level in the liquid reservoir can be conducted. Further, in case of the semiconductor element having a length extending at least with a perpendicular component of direction to the plane level of the liquid even a more discrete measurement of the level of the liquid in the liquid reservoir is possible in that the cooling effect of the liquid is found to be lower or higher, depending on the amount of the length of the semiconductor being immersed into the liquid. In such case, the fluid level sensor may even output a sort of analogue signal indicating the exact position of the level of the liquid inside the liquid reservoir.

In this embodiment, it is further preferred that the housing extends in a longitudinal direction along a longitudinal axis, wherein the exit opening is arranged at one end of said housing with respect to said longitudinal axis and the semiconductor element is positioned inside said liquid reservoir to be immersed in and cooled by said liquid inside said liquid reservoir, wherein said semiconductor element is not immersed in said liquid inside said liquid reservoir if the liquid level falls below a predetermined minimum liquid level threshold with the housing being oriented in a usual operational alignment range, said usual operational alignment range being defined by an orientation of said longitudinal axis in an angular range of +/−45°, +/−30°, +/−15° in relation to a horizontal plane and/or an angular rotation about said longitudinal axis in a full range of 360° or a limited range of +/−45°, +/−30°, +/−15° in relation to horizontal plane making reference to a regular angular position of 0° to said horizontal plane about said longitudinal axis. According to this embodiment, the position of the semiconductor is selected such that under usual operational orientation of the vaporizing device the detection of the level can be safely indicated. It is understood that the range of angular orientation and rotational orientation of the device may be adapted as described beforehand in relation to the capacitor-type of the fluid level sensor.

It is further preferred that said semiconductor element is a positive temperature coefficient (PTC) thermistor. A PTC thermistor is particularly suited for a precise measurement of the change of resistance depending on the cooling effect provided by the liquid if the semiconductor is immersed into the liquid or not.

A further aspect of the invention is a liquid reservoir adapted for being equipped to a vaporizing device as described beforehand, wherein said liquid reservoir comprises a fluid level sensor which is configured like the fluid level sensor described beforehand, in particular as a fluid level sensor functioning as a capacitor or a semiconductor as described beforehand. According to this embodiment, the fluid level sensor is provided as a part of a replacement liquid reservoir and thus will be replaced each time if the liquid reservoir is replaced which ensures a safe function of the fluid level sensor over the time of use of the liquid inside the liquid reservoir. Further, a malfunction of a vaporizing device is prevented due to the installation and use of liquid reservoirs which do not fulfil the requirements of design, volume of the vaporizing device using the signal of a fluid level sensor associated with the liquid reservoir for control of the vaporizer.

BRIEF DESCRIPTION OF THE DRAWINGS

Preferred embodiments of the invention are explained with reference to the figures. In the figures:

FIG. 3 shows a longitudinal sectional view of a part of a vaporizing device according to the invention according to a second embodiment; and FIG. 4 shows a longitudinal sectional view of a part of a vaporizing device according to the invention according to a third embodiment.

DETAILED DESCRIPTION OF THE EMBODIMENTS

Figure 1:
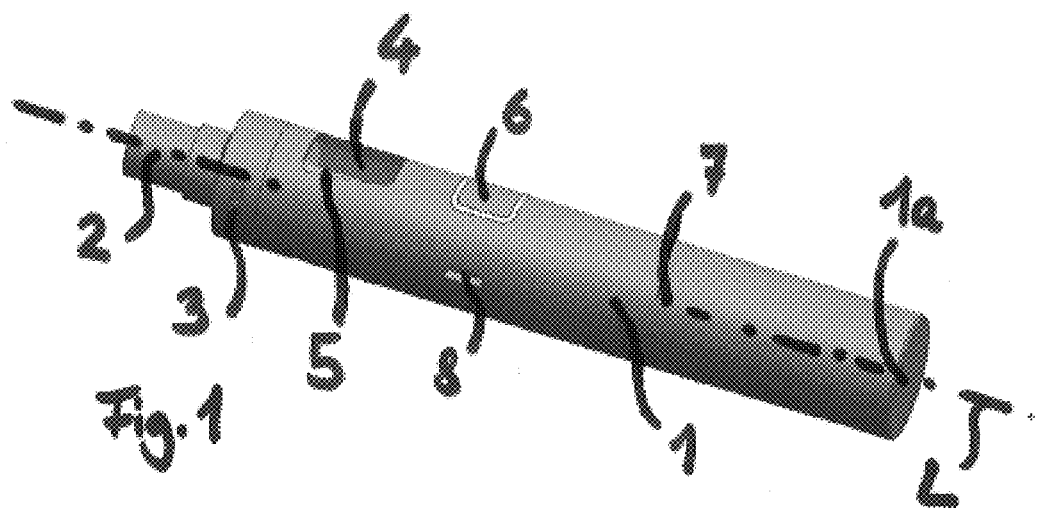
FIG. 1 shows a perspective view of an electronic cigarette according to the invention.

Making reference to FIG. 1 an electronic cigarette comprises a housing 1 extending along a longitudinal, rotational axis L. The housing 1 is shown to be cylindrical, however, other geometrical dimensions like a square or cubical design may apply as well. The housing may be a single part, a two part, or a multipart housing. A mouthpiece 2 constituting the outlet opening is positioned at one end of the housing 1. The other end of the housing is closed by a frontal cover lid 1a. An air inlet 3 is provided at the housing 1. A liquid reservoir 4 is provided inside the housing 1, which may comprise a replaceable or refillable liquid tank. An atomizer 5 is provided inside said housing 1 being in fluid connection with the air inlet 3, the liquid reservoir 4, and the outlet opening. Further, a push button 6 for activating the atomizer 5 is provided at the outside of the housing 1, while it is understood that the atomizer 5 may be activated automatically, e.g., by a sensor detecting flow or under-pressure at the air outlet to start the atomizer 5 if the user draws air out of the outlet opening. Finally, a rechargeable battery 7 is arranged inside the housing which may be recharged via a socket 8.

Figure 2:
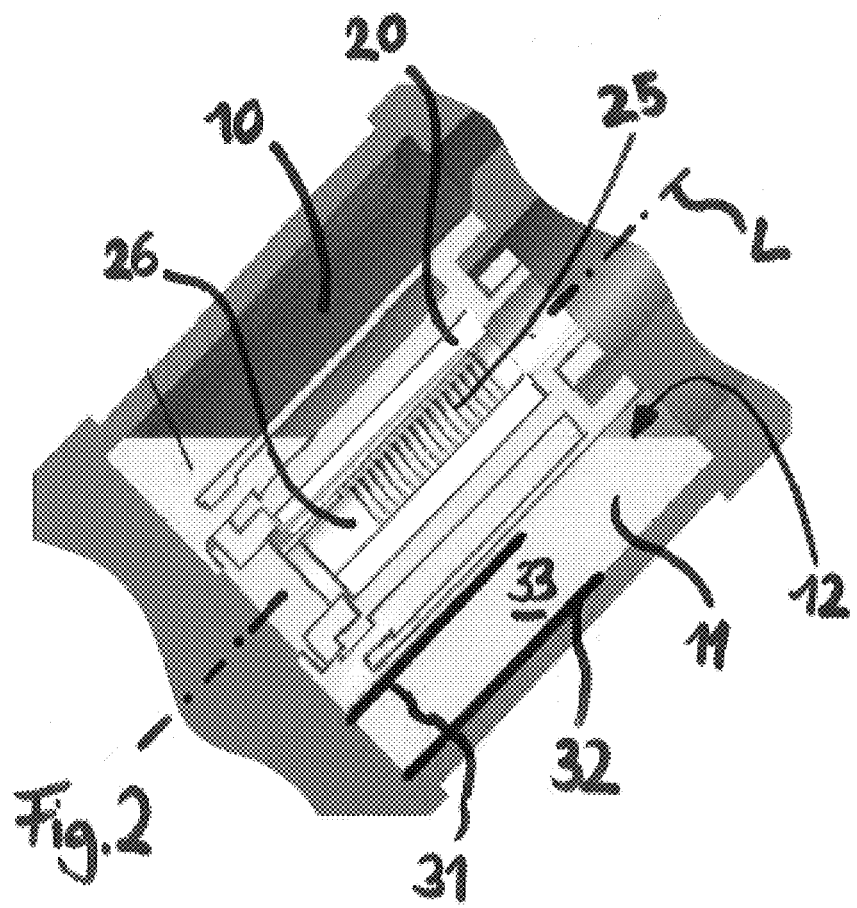
FIG. 2 shows a longitudinal sectional view of a part of a vaporizing device according to the invention according to a first embodiment.

Making reference now to FIG. 2, a vaporizing device is shown in a partial view, wherein a liquid reservoir 10 having a cylindrical geometry is incorporated in the vaporizing device. Inside the liquid reservoir 10 a vaporizer 20 comprising a spirally wound heating wire 25 is positioned. The liquid 11 inside the liquid reservoir 10 may enter a core 26 around which the wire 25 is wound and thus may be heated by the heating wire 25. The user will draw outside air through the vaporizer and the heated liquid will vaporize and partially mix with said air drawn through the vaporizer by forming small liquid droplets and this mix of vaporized liquid, droplets, and air will be drawn by the user to an exit opening of the vaporizing device and thus can be inhaled when exiting said exit opening.

Inside the liquid reservoir 10 a first electrical conductor element 31 and a second electrical conductor element 32 are positioned. The first and second electrical conductor elements 31, 32 are of a semi-cylindrical shape and are concentrically arranged about a longitudinal axis L defined by the cylindrical shape of the liquid reservoir 10. The first and second electrical conductor elements 31, 32 are arranged in a distance from each other such that an electrical insulating space 33 with a constant thickness is positioned between the first and the second electrical conductor element 31, 32. This insulating space 33 is filled with liquid 11, as can be seen from FIG. 2, with the level 12 of the liquid 11 being as high as shown in the filling condition of FIG. 2. The electrical conductor elements 31, 32 and the insulating space form distanced electrodes of a capacitor.

The liquid 11 may be insulating such that a direct contact with the electrically conducting electrodes formed by the electrical conductor elements 31, 32 may be realized. In case of the liquid 11 being electrically conducting, one or both of the electrical conductor elements 31, 32 may comprise an insulating surface layer such that a direct electrical path between the two electrodes is not established. In both cases, a change of the amount of liquid 11 present in the insulating space 33 between the two electrodes will change the capacity of the capacitor formed thereby and thus will allow to calculate a filling rate of the liquid reservoir 10.

In case that the liquid 11 is consumed to a large extent it is apparent that the insulating space 33 between the first and the second electrical conductor element 31, 32 will not be filled only by the liquid 11, but will be filled partially by the liquid and partially by air inside the liquid reservoir. In such case, the capacity of the capacitor formed by the first and second electrical conductor element 31, 32 and the insulating space 33 between these conductor elements will change and this change of capacity may be detected by a control unit. Thus, the decreased level of the liquid 11 can be detected as a direct correlation to the capacity of the capacitor formed by the first and the second electrical conductor element 31 32.

It can be further understood that in case that the vaporizing device is rotated about 180° about the longitudinal, rotational axis L, the insulating space 33 between the first and the second electrical conductor element 31, 32 will not be filled with liquid only, although the amount of liquid in the liquid reservoir 10 did not decrease. In such an orientation of the vaporizing device wherein a sufficient entry of the liquid 11 into the vaporizer may not be guaranteed, a decreased level will be detected by the fluid level sensor formed by the first and second electrical conductor element 31, 32 and thus a low-level-signal will be output by said fluid level sensor in the same way as if the fluid level would have decreased with the correct orientation of the vaporizing device as shown in FIG. 2.

FIG. 3 shows an embodiment wherein a first electrical conductor element 131 is positioned outside a liquid reservoir 110 having a cylindrical wall 113 which is generally designed similar to the liquid reservoir 10 of the first embodiment and incorporates a vaporizer 120 similar to the vaporizer 20 of the first embodiment. The first electrical conductor 131 is formed as a metal foil and wound around the cylindrical liquid reservoir about an angular range of more than 45°, more than 90°, more than 180°, or even more about the rotational axis L. The liquid 111 inside the liquid reservoir 110 is in contact with a second electrical conductor element 132 provided inside the liquid.

The first electrical conductor element 131, the second electrical conductor 132, and the liquid form a capacitor. Whilst it is understood that in the first embodiment the liquid may preferably be electrically insulating to form the capacitor with both electrical conductor elements 31, 32 being in direct contact with the liquid, the liquid employed in the second embodiment may be electrically insulating or electrically conductive. In the first case, the capacitor is formed by the first and the second electrical conductor elements 31, 32 with the liquid acting as an insulator and a change of the level of the liquid will affect the capacity of the capacitor which thus is an indicator of the position of the level inside the liquid reservoir. In the latter case with the liquid being electrically conductive, the liquid will form one of the electrodes of the capacitor and the insulator of the capacitor will be formed by the wall 113 of the liquid reservoir 110. In this case, the capacity will change depending on the level of the liquid due to the size of the electrode formed by the liquid will change depending on the level of the liquid. Thus, in the same effect, the capacity of the capacitor will be an indicator of the level of the liquid inside the liquid reservoir.

It is understood that as an alternative embodiment the second electrical conductor 132 may be omitted and the first electrical conductor 131 may be embodied as a component being divided into two sections which are electrically insulated from each other. The section may be adjacent to each other such that the first section is wound in a first angular region, e.g., 0°-45° and the second section is wound in a second angular region, e.g., from 46°-90° with the region from 45°-46° serving as an insulator. The section may as well be opposed to each other at the circumference of the liquid reservoir. In this embodiment, the two sections form the two electrodes of a capacitor with the liquid inside the tank forming a part of the insulating barrier between the electrodes and thus influencing the capacity of the capacitor.

FIG. 4 shows a third embodiment with a semiconductor 230 being employed as a fluid level sensor. The semiconductor 230 is positioned inside a liquid reservoir 210 which is similar to the liquid reservoir 10 of the first embodiment. In the same way, a vaporizer 220 is positioned inside the liquid reservoir 210 with the vaporizer 220 being similar to the vaporizer 20 of the first embodiment.

The semiconductor 230 is connected to a control unit 235 via two wires and the control unit supplies an electrical current to the semiconductor inducing a small heating effect in the semiconductor 230. As can be seen, the semiconductor 230 is immersed into the liquid inside the liquid reservoir 210 and thus the liquid cools the semiconductor in the condition shown in FIG. 3. Thus, the temperature of the semiconductor 230 will be close to the temperature of the liquid, and the semiconductor 230 will have a specific electrical resistance under this temperature.

In case that the level of the liquid inside the liquid reservoir 210 falls due to consumption of the liquid or in case that the orientation of the vaporizing device in relation to the direction of gravity changes by, e.g., a rotation of the vaporizing device about the rotational axis 201 or a rotation of the vaporizing device in relation to a horizontal plane the semiconductor 230 may no longer be immersed into the liquid but rather reach out of the liquid into the air inside the liquid reservoir. In this case, the cooling effect of the semiconductor 230 by the liquid will no longer be present and the temperature of the semiconductor 230 will rise. This rise in temperature will affect an increase of the electrical resistance of the semiconductor 230 which can be detected by the control unit 235. This rising electrical resistance of the semiconductor 230 will, thus, be a safe indicator of the dropped level of the liquid inside the liquid reservoir or an incorrect orientation of the vaporizing device for proper operation.

The invention claimed is:
1. A vaporizing device for consuming a stimulant or a pharmaceutical substance by inhaling a vapour comprising:
   an elongated cylindrical housing having:
      an exit opening provided at one end of the housing;
      a vaporizer connected to the exit opening via a vapour conduit, the vaporizer having an electrically driven heating unit and a liquid exposure section heated by the heating unit to vaporize a liquid in the liquid exposure section;
      a liquid reservoir adapted to contain the liquid connected to the liquid exposure section via a liquid conduit; and
      an electrical energy storage unit electrically connected to the heating unit; and
   an electrical fluid level sensor associated with the liquid reservoir, the fluid level sensor being arranged and adapted to produce a low-level-signal if a liquid level of the liquid within the liquid reservoir is below a predetermined threshold;

wherein the housing extends in a longitudinal direction along a longitudinal axis, and wherein the exit opening is arranged at one end of the housing with respect to the longitudinal axis and the fluid level sensor is adapted and arranged to produce the low-level signal both if the level inside the liquid reservoir falls below the minimum level threshold or if the housing is not being oriented in a usual operational alignment range, the usual operational alignment range being defined by an orientation of the longitudinal axis in an angular range of +/−45° in relation to a horizontal plane, and wherein the usual operational alignment range is further defined by an angular rotation about the longitudinal axis of +/−45° in relation to a predetermined angular position about the longitudinal axis.

2. The vaporizing device of claim 1, wherein the usual operational alignment range being defined by an orientation of the longitudinal axis in an angular range of +/−30° in relation to a horizontal plane and the usual operational alignment range is further defined by an angular rotation about the longitudinal axis of +/−30° in relation to a predetermined angular position about the longitudinal axis.

3. The vaporizing device of claim 2, wherein the usual operational alignment range is further defined by an angular rotation about the longitudinal axis of +/−15° in relation to a predetermined angular position about the longitudinal axis.

4. The vaporizing device of claim 1, further comprising:
a control unit coupled to the fluid level sensor and to the heating unit for signal transmission, wherein the control unit is adapted to reduce the supply of electrical energy by at least 40% to reduce the supply of electrical energy to the heating device if the control unit receives the low-level-signal from the fluid level sensor.

5. The vaporizing device of claim 1, further comprising:
a control unit arranged inside the housing and coupled to the fluid level sensor and to an optical or acoustical user interface for signal transmission, wherein the control unit is adapted to control the optical or acoustical user interface for outputting an optical or acoustical signal, respectively, upon receipt of the low-level-signal by the control unit.

6. The vaporizing device of claim 1, wherein the liquid level sensor comprises at least one semiconductor element, wherein the liquid level sensor is adapted to determine a resistance of the semiconductor element and to output the low-level-signal depending on the resistance falling below a predetermined minimum threshold or rising above a predetermined maximum threshold, and wherein the semiconductor element is electrically connected to the electrical energy storage unit and is supplied with electrical energy.

7. The vaporizing device of claim 6, and the exit opening is arranged at one end of the housing with respect to the longitudinal axis,
the semiconductor element is positioned inside the liquid reservoir to be immersed in and cooled by the liquid inside the liquid reservoir, and
the semiconductor element is not immersed in the liquid inside the liquid reservoir if the liquid level falls below a predetermined minimum liquid level threshold with the housing being oriented in the usual operational alignment range, the usual operational alignment range being defined by an orientation of the longitudinal axis in an angular range of +/−45° in relation to a horizontal plane, and wherein the usual operational alignment range is further defined by an angular rotation about the longitudinal axis of +/−45° in relation to a predetermined angular position about the longitudinal axis.

8. The vaporizing device of claim 6, wherein the semiconductor element is a PTC thermistor.

9. The vaporizing device of claim 1, wherein the fluid level sensor is a capacity detecting sensor forming a capacitor, wherein the capacity is dependent upon the fluid level in the liquid reservoir.

10. The vaporizing device of claim 9, wherein an electrode of the capacitor is provided by an electrical plane element, or wherein a first and a second electrode of the capacitor are provided by at least two electrical plane elements, respectively, and
wherein each of the electrical plane elements comprise a metallic sheet or a metallic foil.

11. The vaporizing device of claim 9, wherein a first and second electrode of the capacitor are arranged in a parallel arrangement to each other, such that the first and second electrode are arranged in a concentrical arrangement about an axis.

12. The vaporizing device of claim 11, wherein the axis is the longitudinal axis of the housing.

13. The vaporizing device of claim 9, wherein at least one of a first and a second electrode of the capacitor, defined by a first and second conductor element, respectively, are positioned inside the liquid reservoir and are in direct electrical contact with the liquid inside the liquid reservoir.

14. The vaporizing device of claim 9, wherein the liquid reservoir comprises a section with a cylindrical shape about a longitudinal axis of the liquid reservoir, and wherein at least one of a first and a second electrode of the capacitor form a cylindrical shell about the longitudinal axis of the liquid reservoir.

15. The vaporizing device of claim 1, wherein the fluid level sensor comprises at least one electrical conductor element and a further electrical conductor element and the fluid level sensor is adapted to determine a capacity of a capacitor defined by a first electrode formed by the electrical conductor element, a second electrode formed by the further electrical conductor, and an electrically insulating space arranged between the first and second electrode, wherein the low level sensor is adapted to detect a capacity of the capacitor and the low-level-signal is generated depending on the capacity falling below a predetermined minimum threshold or rising above a predetermined maximum threshold, and wherein the insulating space is at least partially defined by a region of the liquid reservoir.

16. The vaporizing device of claim 15, wherein the first and second electrode are arranged inside the liquid reservoir and in direct contact with the liquid, and separated and electrically insulated by the electrically insulating space, wherein the fluid level sensor is adapted to measure the capacity of the capacitor defined by the two electrical conductor elements and the electrically insulating space, wherein the low-level-signal is generated depending on the capacity falling below a predetermined minimum threshold or rising above a predetermined maximum threshold, and wherein the insulating space is at least partially filled by the liquid inside the liquid reservoir.

17. The vaporizing device of claim 15, wherein the first and second electrode are arranged inside or outside the liquid reservoir and are insulated from the liquid and separated by a space, and wherein the fluid level sensor is adapted to measure the capacity of the capacitor defined by the electrodes and the electrically insulating space, wherein the low-level-signal is generated depending on the capacity falling below a predetermined minimum threshold or rising above a predetermined maximum threshold, wherein the space is at least partially filled by liquid inside the liquid reservoir.

18. The vaporizing device of claim 1, wherein the fluid level sensor comprises a first electrical conductor element arranged adjacent to the liquid reservoir and electrically insulated from the liquid inside the liquid reservoir to form a first electrode of a capacitor and wherein a further electrical conductor is provided by a further conductor element being in direct electrical contact with the liquid contained in the liquid reservoir to form a second electrode of the capacitor, wherein the low level sensor is adapted to detect a capacity of the capacitor and the low-level-signal is generated depending on the capacity falling below a predetermined minimum threshold or rising above a predetermined maximum threshold, and wherein the insulating space is at least partially provided by a region of the liquid reservoir.

19. A liquid reservoir adapted to contain a liquid for a vaporizing device, the vaporizing device comprising an elongated cylindrical housing having:
- an exit opening provided at one end of the housing;
- a vaporizer connected to the exit opening via a vapour conduit, the vaporizer having an electrically driven heating unit and a liquid exposure section that is heated by the heating unit to vaporize the liquid in the liquid exposure section;
- a liquid conduit connecting the liquid reservoir to the liquid exposure section; and
- an electrical energy storage unit electrically connected to the heating unit;

wherein an electrical fluid level sensor is associated with the liquid reservoir, the fluid level sensor being arranged and adapted to produce a low-level-signal if a liquid level of the liquid within the liquid reservoir is below a predetermined threshold; and wherein the housing extends in a longitudinal direction along a longitudinal axis, and wherein the exit opening is arranged at one end of the housing with respect to the longitudinal axis and the fluid level sensor is adapted and arranged to produce the low-level signal both if the level inside the liquid reservoir falls below the minimum level threshold or if the housing is not being oriented in a usual operational alignment range, the usual operational alignment range being defined by an orientation of the longitudinal axis in an angular range of +/−45° in relation to a horizontal plane; and wherein the usual operational alignment range is further defined by an angular rotation about the longitudinal axis of +/−45° in relation to a predetermined angular position about the longitudinal axis.

* * * * *